United States Patent
Nau, Jr. et al.

(10) Patent No.: US 8,888,775 B2
(45) Date of Patent: Nov. 18, 2014

(54) SURGICAL FORCEPS INCLUDING SHAPE MEMORY CUTTER

(75) Inventors: William H. Nau, Jr., Longmont, CO (US); David M. Garrison, Longmont, CO (US); Kathy E. Rooks, Aurora, CO (US); Edward M. Chojin, Boulder, CO (US); Jessica E. C. Olson, Frederick, CO (US)

(73) Assignee: Covidien LP, Mansfield, MA (US)

( * ) Notice: Subject to any disclaimer, the term of this patent is extended or adjusted under 35 U.S.C. 154(b) by 1049 days.

(21) Appl. No.: 12/853,896

(22) Filed: Aug. 10, 2010

(65) Prior Publication Data
US 2012/0041438 A1    Feb. 16, 2012

(51) Int. Cl.
A61B 18/14    (2006.01)
A61B 18/00    (2006.01)
A61B 17/00    (2006.01)

(52) U.S. Cl.
CPC ... *A61B 18/1445* (2013.01); *A61B 2018/00196* (2013.01); *A61B 2018/1475* (2013.01); *A61B 2018/1452* (2013.01); *A61B 2018/0063* (2013.01); *A61B 2018/00595* (2013.01); *A61B 2018/144* (2013.01); *A61B 2018/00589* (2013.01); *A61B 2018/00428* (2013.01); *A61B 2017/00867* (2013.01)
USPC .......................................................... 606/49

(58) Field of Classification Search
USPC ..................................... 606/49–52
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 09/387,883, filed Sep. 1, 1999.

(Continued)

*Primary Examiner* — Aaron Roane (57) ABSTRACT

A forceps includes a housing having a shaft attached thereto. The shaft has an end effector assembly disposed at a distal end thereof. The end effector assembly includes a pair of jaw members disposed in opposing relation relative to one another. At least one of the jaw members is moveable relative to the other between a spaced apart position and an approximated position for grasping tissue therebetween. At least one shape memory cutting member is coupled to one of the jaw members. The shape memory cutting member(s) is transitionable between a retracted state and an extended state. In the extended state, the cutting member(s) extends between the jaw members to cut tissue disposed therebetween when the jaw members are in the approximated position.

11 Claims, 4 Drawing Sheets

(56) References Cited

U.S. PATENT DOCUMENTS

| | | | |
|---|---|---|---|
| D402,028 S | 12/1998 | Grimm et al. | |
| D416,089 S | 11/1999 | Barton et al. | |
| D424,694 S | 5/2000 | Tetzlaff et al. | |
| D425,201 S | 5/2000 | Tetzlaff et al. | |
| 6,273,887 B1 * | 8/2001 | Yamauchi et al. | 606/48 |
| D449,886 S | 10/2001 | Tetzlaff et al. | |
| D454,951 S | 3/2002 | Bon | |
| D457,958 S | 5/2002 | Dycus et al. | |
| D457,959 S | 5/2002 | Tetzlaff et al. | |
| D465,281 S | 11/2002 | Lang | |
| D466,209 S | 11/2002 | Bon | |
| 6,656,175 B2 | 12/2003 | Francischelli et al. | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| 7,070,597 B2 | 7/2006 | Truckai et al. | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| 7,270,664 B2 * | 9/2007 | Johnson et al. | 606/51 |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,491,202 B2 | 2/2009 | Odom et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 2003/0018332 A1 | 1/2003 | Schmaltz et al. | |
| 2004/0073238 A1 | 4/2004 | Makower | |
| 2004/0073256 A1 | 4/2004 | Marchitto et al. | |
| 2004/0210282 A1 | 10/2004 | Flock et al. | |
| 2004/0243125 A1 | 12/2004 | Dycus et al. | |
| 2008/0045947 A1 | 2/2008 | Johnson et al. | |
| 2010/0042140 A1 | 2/2010 | Cunningham | |
| 2010/0204697 A1 | 8/2010 | Dumbauld et al. | |
| 2010/0204698 A1 | 8/2010 | Chapman et al. | |
| 2010/0217258 A1 | 8/2010 | Floume et al. | |
| 2010/0249769 A1 | 9/2010 | Nau, Jr. et al. | |
| 2010/0249776 A1 | 9/2010 | Kerr | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 02617 | 12/2005 |
| DE | 20 2007 00931 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

U.S. Appl. No. 09/591,328, filed Jun. 9, 2000.
U.S. Appl. No. 12/336,970, filed Dec. 17, 2008.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.

(56) References Cited

OTHER PUBLICATIONS

U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/822,024, filed Jun. 23, 2010.
U.S. Appl. No. 12/821,253, filed Jun. 23, 2010.
U.S. Appl. No. 12/832,772, filed Jul. 8, 2010.
U.S. Appl. No. 12/833,270, filed Jul. 9, 2010.
U.S. Appl. No. 12/843,384, filed Jul. 26, 2010.
U.S. Appl. No. 12/845,203, filed Jul. 28, 2010.
U.S. Appl. No. 12/846,602, filed Jul. 29, 2010.
U.S. Appl. No. 12/853,896, filed Aug. 10, 2010.
U.S. Appl. No. 12/859,896, filed Aug. 20, 2010.
U.S. Appl. No. 12/859,985, filed Aug. 20, 2010.
U.S. Appl. No. 12/861,198, filed Aug. 23, 2010.
U.S. Appl. No. 12/861,209, filed Aug. 23, 2010.
U.S. Appl. No. 12/876,662, filed Sep. 7, 2010.
U.S. Appl. No. 12/876,668, filed Sep. 7, 2010.
U.S. Appl. No. 12/876,680, filed Sep. 7, 2010.
U.S. Appl. No. 12/876,705, filed Sep. 7, 2010.
U.S. Appl. No. 12/876,731, filed Sep. 7, 2010.
U.S. Appl. No. 12/877,199, filed Sep. 8, 2010.
U.S. Appl. No. 12/877,482, filed Sep. 8, 2010.
U.S. Appl. No. 12/879,505, filed Sep. 10, 2010.
U.S. Appl. No. 12/882,304, filed Sep. 15, 2010.
U.S. Appl. No. 12/895,020, filed Sep. 30, 2010.
U.S. Appl. No. 12/896,100, filed Oct. 1, 2010.
U.S. Appl. No. 12/897,346, filed Oct. 4, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing NeedleStick Injuries in the Operating Room" Sales/Product Literature 2001.
Bergdahl et al. "Studies on Coagulation and the Development of an Automatic Computerized Bipolar Coagulator" J.Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'L Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.

(56) References Cited

OTHER PUBLICATIONS

Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended- EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

SURGICAL FORCEPS INCLUDING SHAPE MEMORY CUTTER

BACKGROUND

The present disclosure relates to surgical instruments. More particularly, the present disclosure relates to surgical forceps for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a forceps including a housing having a shaft attached thereto and an end effector assembly disposed at a distal end of the shaft. The end effector assembly includes a pair of jaw members disposed in opposing relation relative to one another. One (or both) of the jaw members is moveable relative to the other between a spaced apart position and an approximated position for grasping tissue therebetween. One or more shape memory cutting members are coupled to one of the jaw members. The shape memory cutting member(s) is transitionable between a retracted state and an extended state. More specifically, the shape memory cutting member(s) is extended between the jaw members to cut tissue disposed therebetween when transitioned to the extended state.

In one embodiment, the shape memory cutting member is temperature dependent. More specifically, when the shape memory cutting member is heated from an at-rest temperature, the shape memory cutting member is transitioned from the retracted state to the extended state. On the other hand, when the shape memory cutting member is cooled back to the at-rest temperature, the shape memory cutting member is transitioned from the extended state back to the retracted state.

In another embodiment, the shape memory cutting member is adapted to connect to a source of energy for selectively heating the shape memory cutting member to transition the shape memory cutting member from the retracted state to the extended state.

In another embodiment, the shape memory cutting member is formed partially, or entirely, from a Nitinol shape memory alloy. The shape memory cutting member may also be formed from a bimetallic strip of two different materials.

In yet another embodiment, the shape memory cutting member is coiled within a proximal end of one of the jaw members in the retracted state and is uncoiled and extends distally between the jaw members to cut tissue disposed therebetween in the extended state.

In still another embodiment, the end effector assembly includes a plurality of shape memory cutting members coupled to one (or both) of the jaw members. When in the retracted state, each shape memory cutting member is disposed within a recess defined within the jaw member(s). When transitioned to the extended state, each shape memory cutting member extends from the recess and between the jaw members to cut tissue disposed therebetween.

In still yet another embodiment, each end of the shape memory cutting member is engaged to a protrusion extending from one of the jaw members. The shape memory cutting member extends longitudinally along one of the jaw members and is curved inwardly to a position adjacent the jaw member when disposed in the retracted state. In the expanded state, the cutting member is curved outwardly to extend toward the opposed jaw member to cut tissue disposed between the jaw members.

In another embodiment, each jaw member includes an opposed electrically conductive tissue sealing surface adapted to connect to an electrosurgical energy source to communicate energy to tissue disposed between the jaw members to seal tissue disposed therebetween when the jaw members are in the approximated position. In such an embodiment, the shape memory cutting member(s) may be insulated from the tissue sealing surfaces.

The present disclosure also relates to an end effector assembly for use with a surgical forceps. The end effector assembly includes a pair of jaw members disposed in opposing relation relative to one another. One (or both) of the jaw members is moveable relative to the other between a spaced apart position and an approximated position for grasping tissue therebetween. The end effector assembly also includes a shape memory cutting member configured to transition between a coiled state and an expanded state. In the coiled state, the shape memory cutting member is coiled and nested within a proximal end of one of the jaw members. In the expanded state, the shape memory cutting member is uncoiled and extends distally between the jaw members to cut tissue disposed between the jaw members. The shape memory cutting member may be a temperature dependent bimetallic strip formed from two different materials.

The present disclosure further relates to another embodiment of an end effector assembly for use with a forceps. The end effector assembly includes a pair of jaw members disposed in opposing relation relative to one another. One (or both) of the jaw members is moveable relative to the other between a spaced apart position and an approximated position for grasping tissue therebetween. The end effector assembly also includes a plurality of shape memory cutting members. Each shape memory cutting member is coupled to one of the jaw members. The shape memory cutting members are transitionable between a retracted state and an extended state. In the retracted state, each shape memory cutting member is disposed within a recess defined within the jaw member. When transitioned to the extended state, the shape memory cutting members extend from the recesses between the jaw members to cut tissue disposed between the jaw members. The shape memory cutting members may be temperature dependent shape memory alloys (SMAs).

BRIEF DESCRIPTION OF THE DRAWINGS

Various embodiments of the presently disclosed forceps are described herein with reference to the drawings, wherein.

DETAILED DESCRIPTION

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 1:
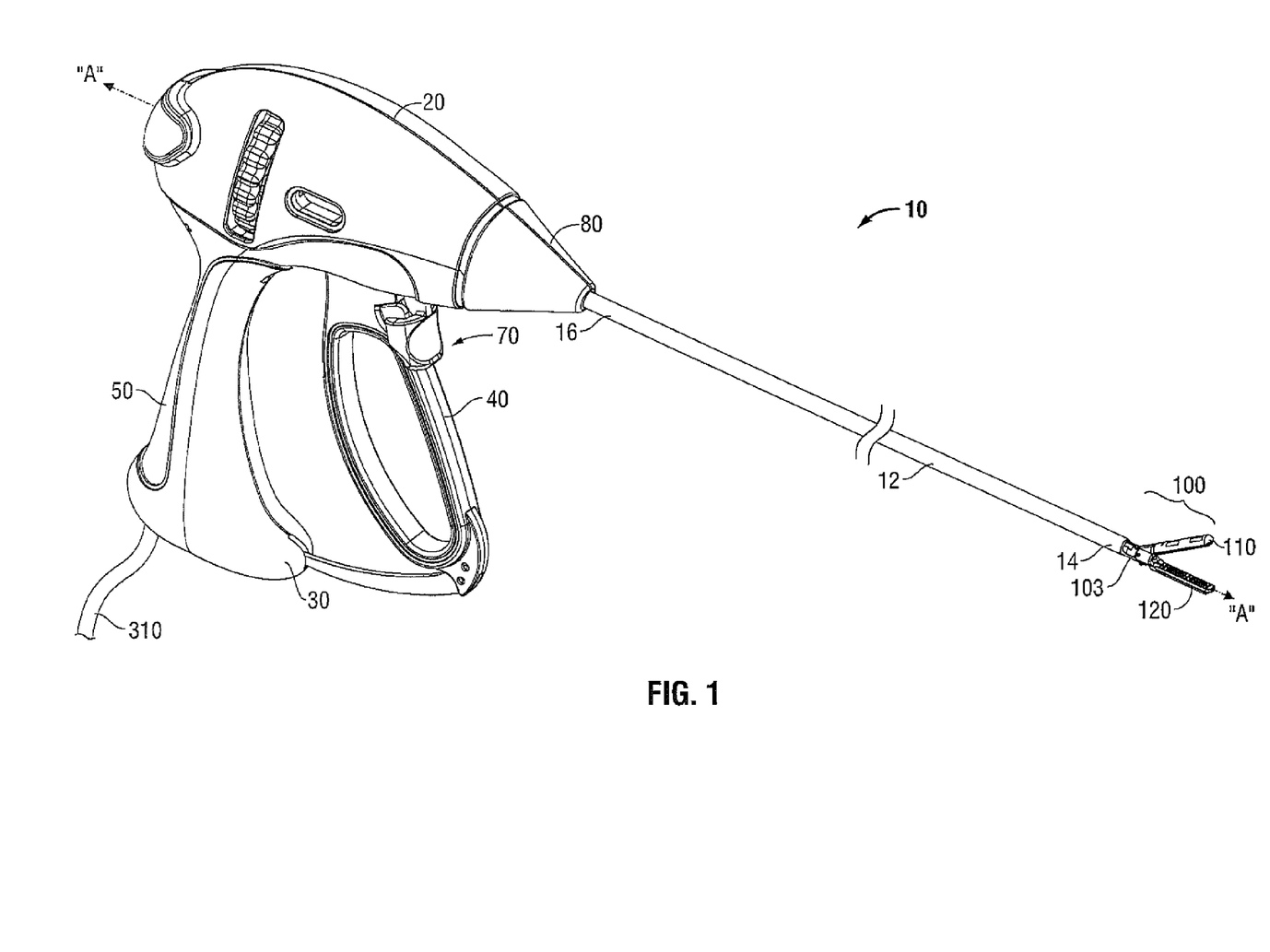
FIG. 1 is a perspective view of a forceps having an end effector assembly in accordance with an embodiment of the present disclosure.

Turning now to FIG. 1, a forceps 10 is provided including a housing 20, a handle assembly 30, a rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. End effector assembly 100 includes a pair of opposing jaw members 110 and 120. End effector assembly 100 is designed as a unilateral assembly, i.e., jaw member 120 is fixed relative to the shaft 12 and jaw member 110 is moveable about a pivot 103 relative to jaw member 120. However, either, or both jaw members 110, 120 may be moveable with respect to the other.

Forceps 10 also includes electrosurgical cable 310 that connects forceps 10 to a generator (not shown). Cable 310 has sufficient length to extend through shaft 12 in order to provide electrical energy to at least one of jaw members 110 and 120 of end effector assembly 100.

With continued reference to FIG. 1, handle assembly 30 includes a fixed handle 50 and a moveable handle 40. Fixed handle 50 is integrally associated with housing 20 and handle 40 is moveable relative to fixed handle 50. Moveable handle 40 of handle assembly 30 is ultimately connected to a drive assembly (not shown) that, together, mechanically cooperate to impart movement of jaw members 110 and 120 between an open, or spaced apart position and a closed, or approximated position. Rotating assembly 80 is integrally associated with housing 20 and is rotatable approximately 180 degrees in either direction about a longitudinal axis "A-A" to correspondingly rotate end effector assembly 100 with respect to housing 20. Housing 20 includes two halves that house the internal working components of the forceps 10.

Various embodiments of end effectors similar to end effector 100 and configured for use with forceps 10 are described in detail with reference to FIGS. 2-10B. Each end effector assembly described hereinbelow includes one or more shape memory cutting members. The respective shape memory cutting members 230, 330, 430 of end effector assemblies 200, 300, 400 (see FIGS. 2, 5 and 8A, respectively) may be temperature dependent shape memory cutting members such as, for example, shape memory alloys (SMAs) or bimetallic strips. Thus, upon heating or cooling of the cutting members, the cutting members are transitioned between a "cold" shape and a "hot" shape.

More specifically, with respect to shape memory alloys (SMAs), the SMA cutting members, e.g., cutting members 230, 330, 430, may be configured for two-way shape memory effect. In other words, the SMA cutting member may be configured to remember two different shapes, a "cold" shape corresponding to a retracted state and a "hot" shape corresponding to an extended state. For purposes herein, $M_f$ is the temperature at which the transition to a martensite phase or stage is finished during cooling, and $A_s$ and $A_f$ are the temperatures at which the transition from the martensite phase to the austenite phase starts and finishes, respectively, during heating. $A_s$ may be determined by the SMA material and composition and, typically, ranges from about 150° C. to about 200° C. $A_f$ may also be determined by the SMA material and composition and/or the loading conditions and, typically, ranges from about 2° C. to about 20° C. or hotter. SMAs suitable for forming cutting members 230, 330, 430 include, but are not limited to, copper-zinc-aluminum-nickel, copper-aluminum-nickel, and nickel-titanium, commonly referred to as Nitinol alloys.

Figure 2:
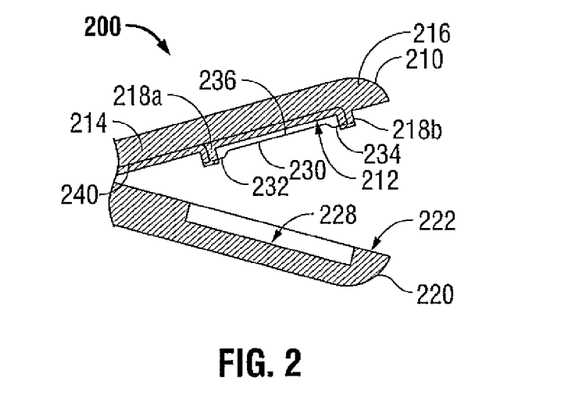
FIG. 2 is an enlarged, perspective view of an end effector assembly for use with the forceps of FIG. 1.
Figure 4A:
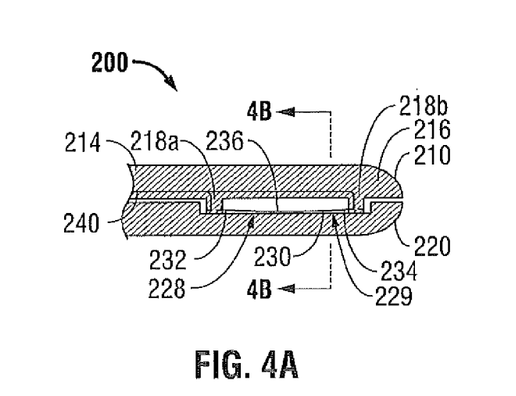
FIG. 4A is a side, cross-sectional view of the end effector assembly of FIG. 2 showing the cutting wire in an extended state.
Figure 5:
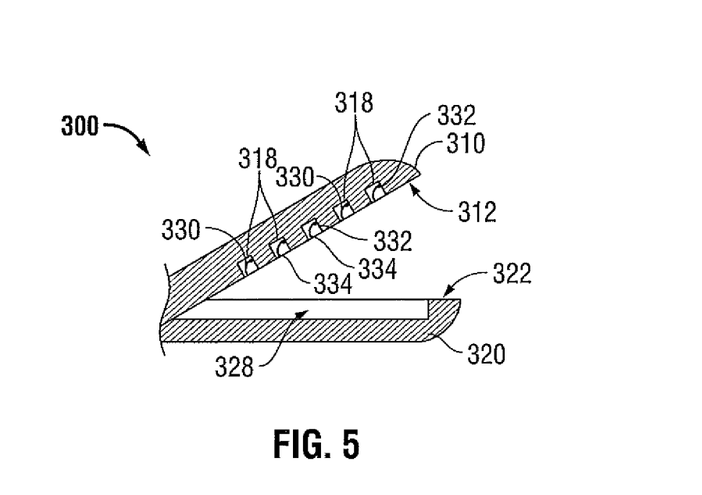
FIG. 5 is an enlarged, perspective view of another end effector assembly for use with the forceps of FIG. 1.
Figure 6A:
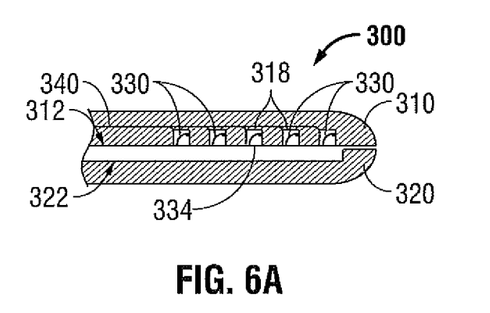
FIG. 6A is a side, cross-sectional view of the end effector assembly of FIG. 5 showing a plurality of cutting wires in a retracted state.
Figure 6B:
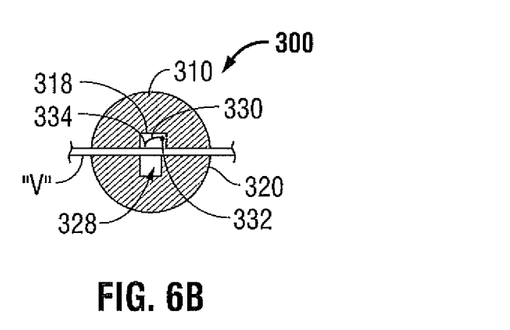
FIG. 6B is a front, cross-sectional view of the end effector assembly of FIG. 5 showing the cutting wires in the retracted state.
Figure 8A:
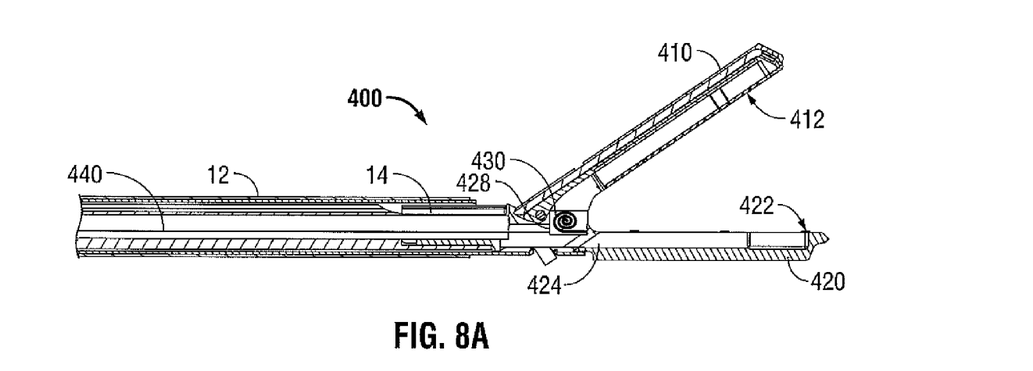
FIG. 8A is a side, cross-sectional view of yet another end effector assembly for use with the forceps of FIG. 1 showing a cutting wire in a coiled, or retracted state and jaw members of the end effector assembly in a spaced apart position.
Figure 10A:
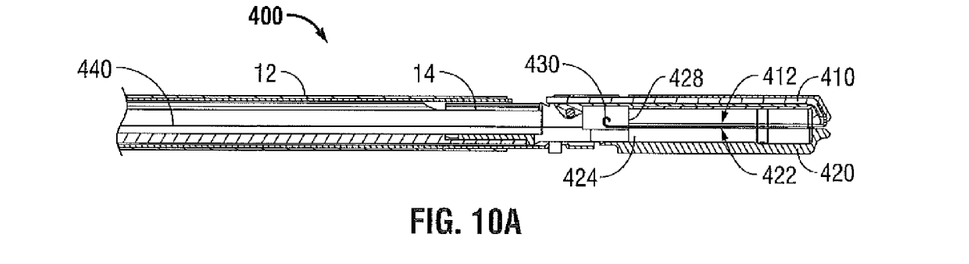
FIG. 10A is a side, cross-sectional view of the end effector assembly of FIG. 8A showing the cutting wire in an extended state, the cutting wire extending between the jaw members.

The SMA cutting members, e.g., cutting members 230, 330, 430, may initially be disposed in a retracted state, as shown in FIGS. 2, 5 and 8A, respectively. This retracted state corresponds to the SMA being in a "cold" shape, that is, the SMA is in a martensite state (e.g., $M_f$, a point below $A_s$). As the SMA "heats up," the SMA eventually reaches an austenite state (e.g., $A_s$) and begins to transition from this "cold" shape to the "hot" shape. During the austenite phase transition (e.g., $A_s \rightarrow A_f$), the SMA continues to expand from the retracted state until it reaches a threshold or final austenite stage ($A_f$), corresponding to the extended state. The extended state of each of cutting members 230, 330, 430 is shown in FIGS. 4A, 6A and 10A, respectively.

If the SMA is allowed to cool (or is cooled), the SMA, as its temperature decreases, will transition from the austenite stage back to the martensite stage such that the SMA cutting members 230, 330, 430 return to the retracted state, shown in FIGS. 2, 5 and 8A, respectively.

Alternatively, as mentioned above, shape memory cutting members 230, 330, 430 of end effector assemblies 200, 300, 400, respectively (see FIGS. 2, 5 and 8A, respectively), may include bimetallic strips. The bimetallic strips are formed from strips of two different metals having different thermal expansion coefficients, e.g., steel and copper or steel and brass. The two strips are aligned side-by-side and fixedly joined together, e.g., by riveting, brazing, welding, etc. Due to the different thermal expansion coefficients of the two joined strips, when the bimetallic strip is heated, the two strips expand at different rates, causing the bimetallic strip to bend, or curve in the direction of the strip having the lower coefficient of thermal expansion.

Accordingly, the bimetallic shape memory cutting members, e.g., cutting members 230, 330, 430, may be configured to expand, curve, or uncoil upon application of heat thereto. More specifically, the bimetallic cutting members may be transitionable between a retracted state, wherein the temperature of the bimetallic cutting member is below a first threshold $T_1$, and an extended state, wherein the temperature of the bimetallic cutting member is above a second threshold $T_2$. At temperatures between the first and second thresholds $T_1$ and $T_2$, respectively, the bimetallic cutting member transitions, e.g., is heated or cooled, between the retracted state and the extended state. The specific shape of the bimetallic cutting members in each of the retracted and extended states as well as the temperature thresholds $T_1$, $T_2$ are determined by the material and composition of the bimetallic strip, the relative thermal expansion rates of the materials and/or by the loading conditions.

One embodiment of an end effector assembly configured for use with forceps 10 is shown in FIGS. 2-4B, generally identified as end effector assembly 200. End effector assembly 200 includes first and second jaw members 210, 220, respectively, disposed in opposing relation relative to one another. One or both jaw members 210, 220 are moveable with respect to the other between a spaced-apart position and an approximated position for grasping tissue therebetween. Each jaw member 210, 220 also includes an opposed electrically conductive sealing surface 212, 222, respectively, such that, when jaw members 210, 220 are moved to the approximated position, tissue is grasped between sealing surfaces 212 and 222. One or both of sealing surfaces 212, 222 may be adapted to connect to a source of electrosurgical energy for conducting energy through tissue to effect a tissue seal.

Referring now to FIG. 2, jaw member 210 includes two protrusions 218 extending therefrom. More particularly, a first protrusion 218a is positioned toward a proximal end 214 of jaw member 210, while a second protrusion 218b is positioned toward a distal end 216 of jaw member 210. Protrusions 218 generally define a rectangular cross-section, although protrusions 218 may define any other suitable cross-section, and extend from sealing surface 212 of jaw member 210 toward jaw member 220. Protrusions 218 may be longitudinally aligned and centered with respect to a width of sealing surface 212. Additionally, protrusions 218 may be formed from an electrically insulative material or, alternatively, may include an insulator (not shown) disposed therearound such that electrical energy supplied to sealing surface 212 of jaw member 210 is not conducted through protrusions 218.

With continued reference to FIG. 2, a shape memory cutting wire 230, e.g., a SMA cutting wire or a bimetallic cutting wire, is coupled to jaw member 210 and extends longitudinally therealong. More specifically, a first end 232 of cutting wire 230 is fixedly engaged to protrusion 218a, while a second end 234 of cutting wire 230 is fixedly engaged to protrusion 218b. Thus, a central portion 236 of cutting wire 230 is suspended between protrusions 218. First and second ends 232, 234, respectively, of cutting wire 230 may be engaged within apertures defined through protrusions 218a, 218b, respectively, or may be fixedly engaged thereto in any other suitable fashion, e.g., adhesion, friction-fitting, clamping, etc.

As shown in FIG. 2, a recess 228 is defined within jaw member 220. More specifically, recess 228 extends longitudinally along sealing surface 222 of jaw member 220 and is generally positioned complementarily to protrusions 218 such that, upon approximation of jaw members 210, 220, protrusions 218 are positionable within recess 228. Alternatively, two separate recesses (not shown) may be provided, each recess corresponding to a respective protrusion 218a, 218b. In fact, recess 228 may be configured in any suitable fashion that permits protrusions 218a, 218b of jaw member 210 to be positionable therein upon approximation of jaw members 210 and 220. Further, as shown in FIG. 3, an internal surface 229 defining recess 228 may be formed from an electrically insulative material, or may be coated with an insulating material such that electrical energy supplied to sealing surface 222 of jaw member 220 is not conducted through internal surface 229 of recess 228.

An electrically insulated wire 240 extends from housing 20, through shaft 12, and into protrusions 218a and/or 218b of jaw member 210 to electrically couple shape memory cutting wire 230 to an electrosurgical energy source, e.g., a generator, and supplies energy, e.g., electrosurgical energy, to shape memory cutting wire 230. Specifically, the electrosurgical energy supplied to shape memory cutting wire 230 may be supplied using variable voltages, frequencies and/or currents and may, for example, heat shape memory cutting wire 230 via resistive heating or RF energy heating. With protrusions 218 of jaw member 210 and internal surface 229 of recess 228 being insulated from sealing surfaces 212, 222 of jaw members 210, 220, respectively, shape memory cutting wire 230 may be independently heated by supplying electrosurgical energy thereto, without effecting sealing surfaces 212, 222. Similarly, supplying electrosurgical energy to sealing surfaces 212, 222, e.g., during tissue sealing, does not directly heat shape member cutting wire 230.

The operation of end effector assembly 200 of forceps 10 is described with reference to FIGS. 2-4B. Initially, as shown in FIG. 2, jaw members 210 and 220 of end effector assembly 200 are disposed in the open, or spaced apart position and shape memory cutting wire 230 is disposed in a retracted state (the "cold" shape). More specifically, shape memory cutting wire 230 defines a curved configuration wherein central portion 236 of cutting wire 230 is curved inwardly towards jaw member 210 from the suspended position between protrusions 218a, 218b. In other words, in the retracted state, shape memory cutting wire 230 is positioned adjacent jaw member 210 along a substantial length of cutting wire 230.

Figure 3A:
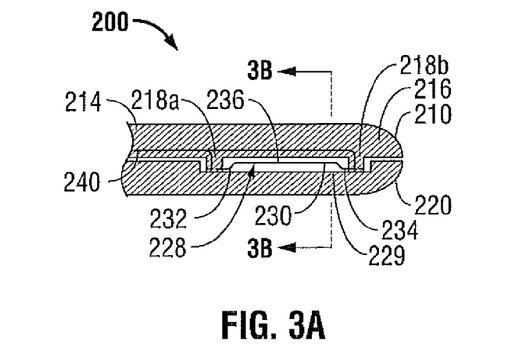
FIG. 3A is a side, cross-sectional view of the end effector assembly of FIG. 2 showing a cutting wire in a retracted state.
Figure 3B:
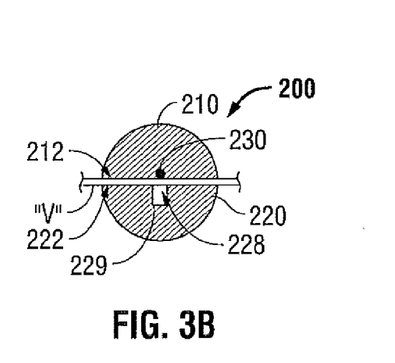
FIG. 3B is a front, cross-sectional view of the end effector assembly of FIG. 2 taken along section line 3B—3B, showing the cutting wire in the retracted state.

Once end effector assembly 200 is positioned with tissue to be sealed and/or cut disposed between jaw members 210, 220, jaw members 210, 220 may be moved to the approximated position, as shown in FIGS. 3A-3B, for grasping tissue between respective sealing surfaces 212, 222. More particularly, tissue, e.g., a vessel "V," may be grasped between sealing surfaces 212, 222 with protrusions 218a and 218b on either side of vessel "V." In other words, tissue to be sealed may be disposed longitudinally between protrusions 218a and 218b.

With continued reference to FIGS. 3A-3B, as jaw members 210, 220 are moved to the approximated position, protrusions 218 of jaw member 210 are positioned within recess (or recesses) 228 of jaw member 220. At this point, shape memory cutting wire 230 remains in the retracted state. In the retracted state, shape memory cutting wire 230 is curved inwardly towards jaw member 210 and is thus disposed above vessel "V," i.e., shape memory cutting wire 230 is not in contact, or is only insubstantially contacting vessel "V" (depending on the diameter of vessel "V").

From the position shown in FIGS. 3A-3B, electrosurgical energy may be applied to sealing surfaces 212, 222 of jaw members 210, 220 to seal tissue disposed between jaw members 210, 220, e.g., to seal vessel "V." With shape memory cutting wire 230 being insulated from sealing surfaces 212, 222, shape memory cutting wire 230 is not directly heated and, thus, remains in the retracted state during tissue sealing.

Figure 4B:
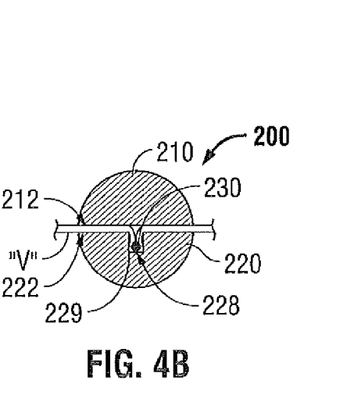
FIG. 4B is a front, cross-sectional view of the end effector assembly of FIG. 2 taken along section line 4B—4B showing the cutting wire in the extended state.

After sealing is complete, sealing surfaces 212, 222 may be deactivated, i.e., the application of electrosurgical energy thereto may be stopped. Electrosurgical or resistive energy may then be applied to shape memory cutting wire 230, e.g., via insulated wires 240, to heat shape memory cutting wire 230. As shape memory cutting wire 230 is heated, shape memory cutting wire 230 is transitioned from the retracted state (FIGS. 3A-3B) to the extended state (FIGS. 4A-4B).

More specifically, in embodiments where cutting wire 230 is a SMA cutting wire, as cutting wire 230 is heated above $A_s$, cutting wire 230 begins to transition, i.e., extend, from the retracted state to the extended state. Similarly, in embodiments where cutting wire 230 is a bimetallic cutting wire, as cutting wire 230 is heated above $T_1$, the metallic strips begin to expand (at different rates), thereby expanding the cutting wire 230 from the retracted state to the extended state.

As cutting wire 230 is expanded to the extended state, central portion 236 of cutting wire 230 is bowed, or curved outwardly from jaw member 210 toward jaw member 220 (the "hot" shape). Accordingly, as central portion 236 of cutting wire 230 is curved, or extended toward jaw member 220, cutting wire 230 is advanced through tissue, e.g., vessel "V," thereby cutting vessel "V" along the previously formed tissue seal, as best shown in FIG. 4B. The relatively thin cutting wire 230 may define a specific cross-sectional configuration, e.g., circular, triangular, hexagonal, diamond-shaped, etc., to facilitate cutting of tissue upon translation of cutting wire 230 with respect to tissue. Further, cutting of tissue may also be facilitated due to the fact that cutting wire 230 is necessarily heated when transitioned to the extended state. In other words, the heating of cutting wire 230 may serve dual purposes: (1) to transition cutting wire 230 between the retracted state and the extended state, and (2) to facilitate cutting of tissue as cutting wire 230 is extended through tissue disposed between jaw member 210, 220.

Once cutting wire 230 has been heated to (or above) the "hot" temperature, $A_f$ (for SMA) or $T_2$ (for bimetallic), cutting wire 230 is fully transitioned to the extended state. As mentioned above, in the extended state, central portion 236 of cutting wire 230 is bowed outwardly from a suspended position between protrusions 218a, 218b to a position adjacent bottom surface 229 of recess 228, as best shown in FIG. 4A.

Once tissue has been cut, shape memory cutting member 230 may be allowed to return, i.e., cooled, from the extended state shown in FIG. 4A to the retracted state shown in FIG. 2.

Another end effector assembly configured for use with forceps 10 is shown in FIGS. 5-7B, generally indicated by reference numeral 300. Similar to end effector assembly 200, end effector assembly 300 includes a pair of jaw members 310, 320 disposed in opposing relation relative to one another and moveable between a spaced apart position and an approximated position for grasping tissue therebetween. Each jaw member 310, 320 includes a respective electrically conductive sealing surface 312, 322 that may be adapted to connect to a source of electrosurgical energy for conducting energy through tissue to effect a tissue seal.

Jaw member 310 includes a plurality of recessed portions 318 defined within sealing surface 312 and positioned longitudinally therealong. Recessed portions 318 may be equally spaced along sealing surface 312 of jaw member 310, or alternatively, may be positioned in any other suitable configuration. Additionally, recessed portions 318 may be longitudinally aligned in one or more columns, or may be staggered with respect to a longitudinal axis of end effector assembly 300. Further, although five (5) recessed portions 318 are shown in FIGS. 5, 6A and 7A, a greater (or fewer) number of recessed portions 318 may be provided.

As best shown in FIG. 6A, a shape memory cutting member 330 is disposed within each recessed portion 318 of jaw member 310. Each shape memory cutting member 330 includes a first, fixed end 332 that is fixedly engaged to jaw member 310 within the respective recessed portion 318, and a second, free end 334. Recessed portions 318 may be formed from an insulated material or may be coated with an insulator to electrically insulate recessed portions 318, and, thus, shape memory cutting members 330, from electrically conductive sealing surfaces 312, 322. Further, free ends 334 of shape memory cutting members 330 may be angled, pointed, or otherwise configured to facilitate translation of free ends 334 of cutting members 330 through tissue.

Initially, shape memory cutting members 330 are disposed in a retracted state (FIGS. 6A-6B) wherein shape memory cutting members 330 are fully disposed within recessed portions 318, i.e., where shape memory cutting members 330 do not extend from jaw member 310. As will be described below, shape memory cutting members 330 are configured to extend from recessed portions 318, between jaw members 310, 320, and at least partially into jaw member 320, to cut, or perforate tissue disposed between jaw members 310, 320 when transitioned, e.g., heated, from the retracted state to the extended state.

Figure 7A:
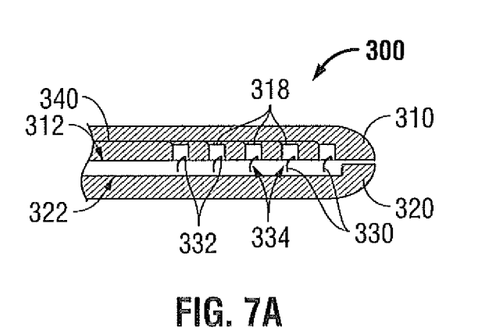
FIG. 7A is a side, cross-sectional view of the end effector assembly of FIG. 5 showing the plurality of cutting wires in an extended state.

With continued reference to FIGS. 6A and 7A, insulated wires 340, or another mechanism for transmitting electrosurgical energy to each of the shape memory cutting members 330 may be provided to selectively transmit electrosurgical energy to heat the shape memory cutting members 330 from the retracted state to the extended state, and thus to transition the cutting members 330 from the retracted state to the extended state for cutting, or perforating tissue disposed between jaw members 310, 320. Electrosurgical energy may be independently applied to cutting members 330 and sealing surfaces 312, 322 of jaw members 310, 320, respectively, i.e., wires (not shown) other than insulated wires 340 may supply electrosurgical energy to sealing surfaces 312, 322, such that the sealing and cutting operations of end effector assembly 300 may be independently and separately activated.

As shown in FIGS. 5, 6A and 7A, jaw member 320 includes a channel 328 defined therein and extending longitudinally along sealing surface 322. Channel 328 is positioned to permit extension of shape memory cutting members 330 therethrough when cutting members 330 are transitioned to the extended state. Alternatively, a plurality of channels 328 may be provided, each channel 328 configured to accept one (or more) of the cutting members 330 therein. Further, channel(s) 328 may be insulated from sealing surface 322 of jaw member 320.

In operation, once end effector assembly 300 is positioned with tissue to be sealed and/or cut disposed between jaw members 310, 320, jaw members 310, 320 may be moved to the approximated position to grasp and seal tissue, e.g., vessel "V," between sealing surfaces 312, 322 of jaw members 310, 320, respectively, as discussed above in relation to end effector assembly 200. Next, electrosurgical energy may be applied, via wires 340, to cutting members 330 to heat, or transition cutting members 330 from the retracted state (FIGS. 5 and 6A-6B) to the extended state (FIGS. 7A-7B).

In embodiments where cutting members 330 are SMA cutting members, cutting members 330 begin to reshape, or extend from the retracted state once cutting members 330 are heated above the at-rest temperature $A_s$. Similarly, in embodiments where cutting members 330 are bimetallic cutting members, cutting members 330 are reshaped, or extended from the retracted state once cutting members 330 are heated above the first threshold temperature $T_1$.

As cutting members 330 are further heated toward the extended state, free ends 334 of cutting members 330 are extended from respective recesses 318 of jaw member 310. More specifically, cutting members 330 are extended between jaw members 310, 320, and eventually into channel(s) 328 defined within jaw member 320, as shown in FIGS. 7A-7B. Thus, as free ends 334 of cutting members 330 are extended at least partially into jaw member 320, cutting members 330 are advanced through tissue, e.g., vessel "V," thereby perforating, or cutting vessel "V" along the previously formed tissue seal. As mentioned above, the configuration of cutting members 330 and/or the heating of cutting members 330 may facilitate translation through and cutting of tissue by each of cutting members 330.

Figure 7B:
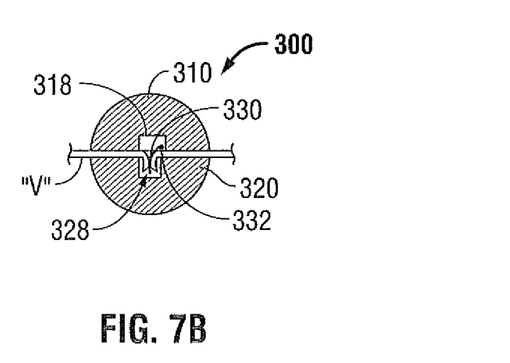
FIG. 7B is a front, cross-sectional view of the end effector assembly of FIG. 5 showing the cutting wires in an extended state.

FIGS. 7A-7B show end effector assembly 300 once cutting members 330 have been heated to the extended state, i.e., once cutting members 330 have been heated to or above the "hot" temperature: $A_f$ (for SMA) or $T_2$ (for bimetallic). In this position, cutting members 330 have fully transitioned from the retracted state to the extended state and, thus, cutting members 330 have extended through and cut tissue disposed between jaw members 310, 320.

Cutting members 330 may be positioned along jaw member 310 such that tissue is perforated when cutting members 330 are transitioned to the extended state, thereby allowing for relatively easy tissue division along the perforations. Alternatively, cutting members 330 may be positioned along jaw member 310 such that the plurality of cutting members 330 divide tissue disposed between jaw members 310, 320 when transitioned to the extended state. For example, if perforating tissue is desired, end effector assembly 300 may be provided with fewer cutting members 330 and/or cutting members 330 may be spaced further apart from one another. On the other hand, if dividing tissue is desired, end effector assembly 300 may be configured with more cutting members 330 and/or cutting members 330 may be more concentrated within a given area.

Once tissue has been cut or preforated, shape memory cutting members 330 may be allowed to return, i.e., cool, from the extended state shown in FIG. 7A to the retracted state shown in FIG. 6A.

Yet another end effector assembly configured for use with forceps 10 is shown in FIGS. 8A-10B, generally indicated by reference numeral 400. Similar to end effector assemblies 200, 300 discussed above, end effector assembly 400 includes a pair of jaw members 410, 420 disposed in opposing relation relative to one another. Jaw member 420 is fixed relative to shaft 12, while jaw member 410 is moveable with respect to jaw member 420 between a spaced-apart position and an approximated position for grasping tissue therebetween. Each jaw member 410, 420 includes an electrically conductive sealing surface 412, 422, respectively, that may be adapted to connect to a source of electrosurgical energy for conducting energy through tissue to effect a tissue seal.

As shown in FIG. 8A, a shape memory cutting member 430 is initially nested, or positioned within proximal end 424 of fixed jaw 420. An insulated cutting member housing 428 may be disposed within proximal end 424 of fixed jaw member 420 to house shape memory cutting member 430 therein when cutting member 430 is in the retracted state (the "cold" shape). Cutting member housing 428 may be nested within jaw member 420 such that, as best shown in FIG. 8A, cutting member 430 is not exposed, i.e., such that cutting member 430 does not extend between jaw members 410, 420, when cutting member 430 is in the retracted state. Further, insulated cutting member housing 428 may be configured to insulate cutting member 430 from sealing surfaces 412, 422 of jaw members 410, 420, respectively.

Figure 8B:
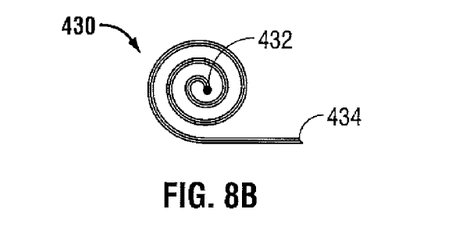
FIG. 8B is an enlarged, side view of the cutting wire of FIG. 8A shown in the retracted state.

FIG. 8B shows shape memory cutting member 430 in the retracted state. As in any of the previous embodiments described herein, shape memory cutting member 430 may be formed from a SMA, a bimetallic strip, or any other suitable thermally activated shape memory material. Shape memory cutting member 430 includes a fixed end 432 and a free end 434. Fixed end 432 is rotatably engaged to cutting member housing 428 via any suitable mechanism, e.g., a pin-aperture engagement. Free end 434 of cutting member 430 may be configured, e.g., angled to define a cutting edge, to facilitate translation of cutting member 430 through tissue disposed between jaw member 410, 420 upon the transition of cutting member 430 from the retracted to the extended state (the "hot" shape). In the retracted state, cutting member 430 is coiled around fixed end 432 such that cutting member 430 is disposed within cutting member housing 428. When heated, shape memory cutting member 430 is configured to uncoil, extending longitudinally and distally between jaw members 410, 420 to cut tissue disposed therebetween. More specifically, an insulated wire 440 coupled to cutting member 430 and extending through shaft 12 may be adapted to connect to a source of electrosurgical or resistive energy for heating shape memory cutting member 430 and, thus, for transitioning cutting member 430 from the "cold" shape to the "hot" shape. Electrosurgical energy may be provided, via wire 440, to cutting member 430 independently of sealing surfaces 412, 422. In other words, separate wires (not shown) may be provided to supply electrosurgical energy to sealing surfaces 412, 422 of jaw member 410, 420 and to cutting member 430 such that each may be independently activated.

Sealing surfaces 412 and/or 422 of jaw members 410, 420, respectively, may include channels (not shown) defined therein to accommodate extension of cutting member 430 therethrough. Alternatively, cutting member 430 may be configured to extend between jaw members 410, 420, obviating the need for the channel(s) (not shown).

Figure 9:
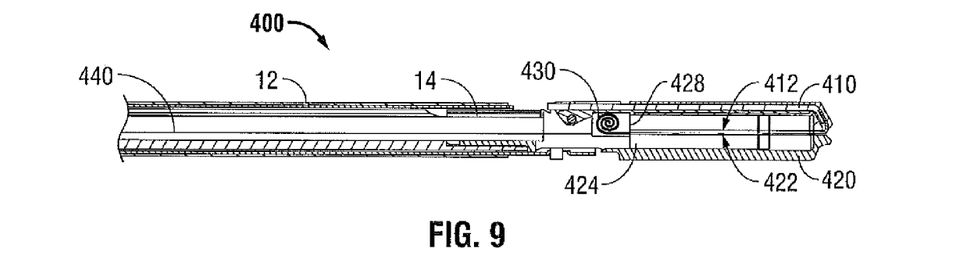
FIG. 9 is a side, cross-sectional view of the end effector assembly of FIG. 8A showing the cutting wire in the retracted state and the jaw members in an approximated position.

In operation, jaw members 410, 420 may be moved to the approximated position (FIG. 9), to grasp and seal tissue, e.g., vessel "V," between sealing surfaces 412, 422 of jaw members 410, 420, respectively. As shown in FIG. 9, during tissue sealing (or when jaw members 410, 420 are approximated to grasp tissue therebetween), cutting member 430 remains in the "cold" shape, positioned within insulated cutting member housing 428.

Figure 10B:
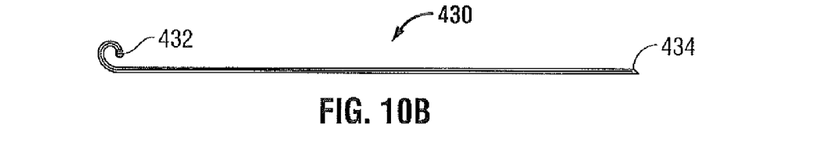
FIG. 10B is an enlarged, side view of the cutting wire of FIG. 8A shown in the extended state.

When it is desired to cut tissue disposed between jaw members 410, 420, electrosurgical energy may be applied, e.g., via wires 440, to cutting member 430 to transition cutting member 430 from the "cold" shape (FIGS. 8A-9) to the "hot" shape (FIGS. 10A-10B).

In embodiments where cutting members 430 are SMA cutting members, cutting member 430 is uncoiled from the "cold" shape upon heating of cutting member 430 above the at-rest temperature A. Similarly, in embodiments where cutting member 430 is a bimetallic strip, cutting member 430 is uncoiled, or extended from the "cold" shape upon heating of cutting member 430 above the first threshold temperature $T_1$.

As cutting member 430 is uncoiled and advanced distally, free end 434 of cutting member 430 is extended distally from cutting member housing 428 between jaw members 410, 420, as shown in FIG. 10A. Accordingly, free end 434 of cutting member 430 is extended between jaw members 310, 320, thereby translating through tissue, e.g., vessel "V," grasped between respective sealing surfaces 412, 422 of jaw members 410, 420, to cut vessel "V." The "hot" cutting member 430 and/or the configuration of free end 434 of cutting member 430 may facilitate the cutting, or dividing of tissue disposed between jaw members 410, 420.

FIG. 10A shows end effector assembly once cutting member 430 has been heated to the "hot" shape, i.e., where cutting member 430 has been heated to $A_f$ (for SMA) or $T_2$ (for bimetallic), such that cutting member 430 is substantially uncoiled and extends between jaw members 410, 420. In this position, as shown in FIG. 10B, cutting member 430 has fully transitioned from the retracted state to the extended state. Allowing cutting member 430 to cool (or cooling cutting member 430) from the "hot" shape (FIGS. 10A-10B) causes cutting member 430 to retract, or recoil back to the "cold" shape (FIGS. 8A-9).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A forceps, comprising:
a housing having a shaft attached thereto, the shaft having an end effector assembly disposed at a distal end thereof, the end effector assembly including:
a pair of jaw members disposed in opposing relation relative to one another, at least one jaw member moveable relative to the other between a spaced-apart position and an approximated position for grasping tissue therebetween; and
a shape memory cutting wire extending longitudinally along one of the jaw members, the shape memory cutting wire having first and second end portions and an intermediate portion, the first and second end portions coupled to the jaw member such that the intermediate portion is suspended therebetween, the shape memory cutting wire transitionable between a retracted state, wherein the intermediate portion is positioned adjacent the jaw member, and an extended state, wherein the intermediate portion extends between the jaw members to cut tissue disposed therebetween.

2. The forceps according to claim 1, wherein the shape memory cutting wire is temperature dependent such that, when the shape memory cutting wire is heated from an at-rest temperature, the shape memory cutting wire is transitioned from the retracted state to the extended state and such that, when the shape memory cutting wire is cooled back to the at-rest temperature, the shape memory cutting wire is transitioned from the extended state back to the retracted state.

3. The forceps according to claim 2, wherein the shape memory cutting wire is adapted to connect to a source of energy for selectively heating the shape memory cutting wire to transition the shape memory cutting wire from the retracted state to the extended state.

4. The forceps according to claim 1, wherein the shape memory cutting wire is formed at least partially from a Nitinol alloy.

5. The forceps according to claim 1, wherein the shape memory cutting wire is formed from a bimetallic strip of two different materials.

6. The forceps according to claim 1, wherein each jaw member includes an opposed electrically conductive tissue sealing surface adapted to connect to an electrosurgical energy source to communicate energy to tissue disposed between the jaw members to seal tissue disposed therebetween when the jaw members are in the approximated position.

7. The forceps according to claim 6, wherein the shape memory cutting wire is insulated from the tissue sealing surfaces.

8. The forceps according to claim 1, wherein, in the retracted state, the intermediate portion of the shape memory cutting wire is bowed inwardly towards the jaw member.

9. The forceps according to claim 1, wherein, in the extended state, the intermediate portion of the shape memory cutting wire is bowed outwardly towards the other jaw member.

10. The forceps according to claim 1, wherein the other jaw member defines a channel that is configured to at least partially receive the intermediate portion of the shape memory cutting wire in the extended state.

11. The forceps according to claim 1, wherein the first and second end portions of the shape memory cutting wire are engaged to proximal and distal protrusions, respectively, of the jaw member.

* * * * *